(12) United States Patent
Dube (10) Patent No.: US 8,052,729 B2
(45) Date of Patent: Nov. 8, 2011

(54) ANTERIOR LUMBAR LAG PLATE

(75) Inventor: Michael A. Dube, Great Falls, MT (US)

(73) Assignee: Stryker Spine (FR)

( * ) Notice: Subject to any disclaimer, the term of this patent is extended or adjusted under 35 U.S.C. 154(b) by 803 days.

(21) Appl. No.: 11/081,954

(22) Filed: Mar. 16, 2005

(65) Prior Publication Data

US 2006/0229618 A1   Oct. 12, 2006

(51) Int. Cl.
*A61B 17/80* (2006.01)

(52) U.S. Cl. .................... 606/289; 606/288; 606/280

(58) Field of Classification Search ............ 606/61, 606/69, 70, 246, 280, 289, 295, 297, 288
See application file for complete search history.

(56) References Cited

U.S. PATENT DOCUMENTS

| | | | |
|---|---|---|---|
| 4,794,918 A * | 1/1989 | Wolter | 606/69 |
| 5,127,912 A | 7/1992 | Ray et al. | |
| 5,609,592 A | 3/1997 | Brumfield et al. | |
| 5,951,558 A * | 9/1999 | Fiz | 606/70 |
| 6,059,829 A | 5/2000 | Schlapfer et al. | |
| 6,228,085 B1 * | 5/2001 | Theken et al. | 606/289 |
| 6,235,034 B1 * | 5/2001 | Bray | 606/71 |
| 6,306,139 B1 * | 10/2001 | Fuentes | 606/70 |
| 6,413,259 B1 * | 7/2002 | Lyons et al. | 606/295 |
| 6,602,255 B1 * | 8/2003 | Campbell et al. | 606/69 |
| 6,793,658 B2 | 9/2004 | LeHuec et al. | |
| 2004/0034356 A1 * | 2/2004 | LeHuec et al. | 606/72 |
| 2004/0193269 A1 * | 9/2004 | Fraser et al. | 623/17.11 |
| 2004/0204712 A1 * | 10/2004 | Kolb et al. | 606/69 |
| 2005/0149027 A1 * | 7/2005 | Campbell et al. | 606/70 |

* cited by examiner

*Primary Examiner* — Eduardo C Robert
*Assistant Examiner* — Julianna N Harvey
(74) *Attorney, Agent, or Firm* — Lerner, David, Littenberg, Krumholz & Mentlik, LLP

(57) ABSTRACT

An anterior lumbar plate for attachment with bone screws to selected vertebrae of a person's spine is combined: (a) with separate L5 and S1 drill guides separately and removably attachable to the lumbar plate, and (b) with lock plates removably attachable to the lumbar plate to prevent unscrewing of installed bone screws. This invention further provides a method for implanting and locking in place the L5 and S1 bone screws. This invention is adaptable for L4-L5, L4-L5-S1, and L5-S1 lumbar plates.

30 Claims, 6 Drawing Sheets

ANTERIOR LUMBAR LAG PLATE

I. BACKGROUND OF THE INVENTION

A. Field of the Invention

The present invention relates to spinal fusions and more particularly to an anterior approach implant system for fixing a stabilizing appliance to the L4-L5, L5-S1 and L4-L5-S1 vertebrae.

B. Prior Art

Over 200,000 spinal fusions are performed each year in the United States, with the L4-L5 and L5-S1 disc spaces being the most commonly fused. The indications for fusion range from traumatic instability to degenerative spinal stenosis. Procedures which require decompression in addition to fusion are most commonly performed posteriorly. Fusions performed for primarily mechanical axial back pain from degenerative disc disease are done anteriorly.

In the past, performing anterior fusion with total disc excision has been problematic without using posterior instrumentation. There was the "cage rage" of the 1990's which lead to high non-union rates and failures. Surgeons then began to perform 360s or anterior and posterior fusions because of the superiority of posterior instrumentation. This subjected patients to long procedures with significant morbidity.

Recently, surgeons have been attempting to perform discectomy and anterior fusion with posterior approaches, such as posterior lumbar interbody fusion (PLIF) and transpedicular lumbar interbody fusion (TLIF). These techniques are difficult and require significant nerve root retraction, which places the root at risk. There has also been a high rate of non-union because of inadequate disc space preparation from the posterior approach. This has led a significant number of surgeons to once again approach this problem anteriorly; however, rather than using a stand-alone technique they are using anterior instrumentation.

The anterior approach allows a more safe and speedy access to the disc and more safe preparation of the disc, resulting in higher fusion rates. Unfortunately, current instrumentation systems for anterior fusion, such as the Danek triangular plate and the Synthese plate, have serious flaws.

The Danek triangular plate is an anterior plate designed for L5-S1 fusion only, with its base having two screw holes for placement in S1 and its top having one hole for screw placement in L5. Because of this triangular structure with one hole at each apex of the triangle, coronal rotation of L5 cannot be controlled.

With the Synthese anterior plate each bone screw has distal portion threads for engagement with the L5 and S1 vertebrae respectively, and proximal portion threads for engagement with the plate. The plate, the screws and the L5 and S1 vertebrae become joined as a unit, and the vertebrae cannot angulate relative to the plate or relative to each other, thus the term "fixed angle device". Because of this construction, the Synthese plate has two significant shortfalls. Firstly, a fixed angle device does not allow any dynamic loading in compression and may stress shield the graft, possibly leading to non-union. Secondly, the locking mechanism with the Synthese plate fixes the screw to the plate and does not allow the plate to be lagged to the bone securely. This can lead to prominence of the plate, which can be a problem in this location, since the plate is placed under the great vessels at L4-L5. Also, the surgeon has no feel for the purchase of the screws to the bone.

III. SUMMARY OF THE NEW ANTERIOR LUMBAR LAG PLATE INVENTION

The design of the new Anterior Lumbar Lag Plate (hereinafter "lumbar plate") takes into account the uses for the plate and the flaws of its predecessors, and maximizes its effectiveness as an anterior lumbar fusion device. The new lumbar plate is used in lag mode wherein the screws are placed in a mode that allows for dynamic compression, but no distraction and therefore this plate also functions as a tension band.

More specifically, when the L5-S1 and bone graft therebetween go into compression, the bone screw extending with clearance through the lumbar plate can incline downward a few degrees while the lumbar plate fixed to S1 remains substantially unmoved. This allows a dynamic compression load on the bone graft which replaced the disc, and enhances better spinal fusion between L5,S1 and the bone graft.

Three embodiments of the new lumbar plate are disclosed herein, to be used respectively at L4-L5, L5-S1 or L4-L5-S1. Each of these lumbar plates can be utilized from a transabdominal or retroperitoneal approach. Each plate is preferably made of titanium which allows for accurate postoperative imaging with MRI, if needed.

The new instrumentation allows for use of a single step drill or awl through a drill guide, followed by placement of each self-threading screw through a drill guide. This drill guide does not have to be moved or changed in position between the steps of forming the holes and placing the screws. This avoids the inconvenience and requirement in prior systems of removing the drill guide before placing the screws. This also avoids the risk of incorrect final alignment of holes of the plate and the vertebrae. The new lumbar plate and method of placement is very surgeon friendly, shortens operative time and adds accuracy. Also, by allowing use of a drill or an awl as alternate methods of screw placement, the surgeon has a choice of the techniques for preparing the bone to accept a screw, depending on the condition and structure of the vertebra bone made visible by the surgery.

In patients with relatively hard bone structure, drilling before screw placement can easily accomplish secure purchase. In osteroporotic bone, an awl may be selected to compact the bone around the screw hole before screw placement for achieving more secure screw purchase.

In further describing these embodiments, the following terminology will be employed. Anterior or anterior surface means the front side of the spine facing foreword toward the rib cage, chest and front of the stomach, and posterior or posterior surface means the opposite rear side of the vertebral column adjacent a person's back. Also in this description, superior means in the direction of, or closer to the person's head, and inferior means in the direction of, or closer to the person's feet. Proximal and distal mean near and far respectively. Cephalad means toward the head or anterior part. For clarity and convenience lumbar vertebrae L4 and L5 and sacral vertebra S1 will be referred to simply as L4, L5 and S1 respectively.

The present invention further includes a unique locking system to prevent or substantially restrict unscrewing of the bone screws which attach the new lumbar plate to L4-L5, L5-S1 or L4-L5-S1. In the new locking system, a thin plate is fastened to the anterior surface of the lumbar plate where it overlies all or at least a part of the heads of the implanted bone screws. In a first embodiment of this locking system, the exposed anterior surface of the lumbar plate includes a recess or pocket into which the locking plate is positioned, so that the resulting assembly of lumbar plate and locking plate has a generally smooth anterior surface. In a second embodiment of this locking system, the locking plate sits externally of the anterior surface of the lumbar plate but this locking plate still partially or fully overlies the heads of the bone screws and thus prevents these screws from unscrewing. In either embodiment, the posterior side of the locking plate can include optional projections which are extended into the hexagonal recesses of hex head bone screws, where the projections serve to assure proper seating of the lock plate.

The new L5-S1 lumbar plate, which is typical of all three embodiments herein, has top, bottom and middle portions, with a top set of laterally spaced-apart holes for the L5 bone screws, a bottom set of laterally spaced-apart holes for the S1 bone screws, a threaded hole between the two holes of each of said sets of spaced-apart holes, and an aperture vertically between said two sets of spaced-apart holes. Each of said threaded holes has a dual function, first, to receive the screw for releasably securing one of the drill guides to the lumbar plate, and second, to later receive the screw for releasably securing a locking plate to the lumbar plate.

The lumbar plate can be manufactured in three configurations, namely:
 a. a lumbar plate for a single level fusion of L4-L5,
 b. a lumbar plate for a single level fusion of L5-S1 which will have a ridge for localization on the superior end plate of S1, and
 c. a lumbar plate for two level fusion extending across L4-L5-S1 which will have a localization ridge for placement at S1. The respective lumbar plates will have two laterally spaced holes for fixation in L4, two laterally spaced holes for L5, and two laterally spaced holes for S1.

All of these lumbar plates can be made of titanium, which will aide in post operative MRI imaging if necessary. The size of each lumbar plate will be labeled indicating the distance between the centers of the screw holes at each end, namely, between the top and bottom holes. Single level fusion L5-S1 plates will start at 13 mm and range in two-millimeter increments up to 33 mm. Single level fusion L4-L5 plates will range from about 13 mm to 39 mm, and two level L4-S1 plates will have lengths ranging from about 13 mm to 65 mm. The screws utilized will be titanium coarse threaded screws 6.0 mm in diameter and will range in length from about 15 mm to 35 mm.

IV. SUMMARY OF THE IMPLANTATION PROCEDURE FOR THE NEW ANTERIOR LUMBAR LAG PLATE

The method of implantation of the new lumbar plate will be through the anterior approach, which will be either anterior transabdominal or retroperitoneal. The appropriate disc space is exposed, the annulus fibrosis is removed as well as the entire nucleus of the intervetebral disc, and the cartilage end plates are curetted down to bleeding bone. At this time the surgeon's choice of bone graft is placed.

The procedure for the L5-S1 plate, typical for all plates, is as follows. Plate length is selected by placing a plate template over the affected disc space and then choosing the length of the plate. Once the appropriate length plate is chosen, the L5 drill guide is affixed to the plate. Then the plate with attached drill guide for holes in L5 is placed against the anterior vertebral body adjacent L5-S1. The holes may then be drilled or the cortex of the bone punctured with an awl. The drill or awl is removed, and a screw is placed through the guide and advanced into L5 after each hole is formed. The L5 drill guide is then removed with the plate firmly attached to L5, the S1 drill guide is attached to the lumbar plate and the procedure is repeated. The screws placed in S1 are to be subjacent the bony endplate; the screws placed in L5 can be more centrally placed in the vertebral body. X-rays are taken to confirm correct placement of the bone screws. Finally, the locking plates are attached.

The new lumbar plate system is designed to be implanted permanently and need not be removed unless there are other circumstances requiring its removal.

The above is intended merely as a summary of various inventive aspects presented in the present application and is in no way intended to be an exhaustive or all-inclusive recitation of such aspects. Additional aspects, forms, features and embodiments of the present invention will be further described below with regard to the preferred embodiments.

V. BRIEF DESCRIPTION OF THE DRAWINGS

FIG. 14 is a top view in section of the lumbar plate of FIG. 5, showing the top drill guide attached with a drill bit extending only into upper left hole 12a, FIG. 14A is a sectional view similar to FIG. 14, showing the top drill guide attached to the lumbar plate, with a screw installed in upper left hole 12a, and with a drill bit extending into upper right hole 12b.

VI. DETAILED DESCRIPTION OF THE PREFERRED EMBODIMENTS

For convenience and clarity in describing these embodiments, similar elements or components appearing in different figures will have the same reference numbers.

Figure 1:
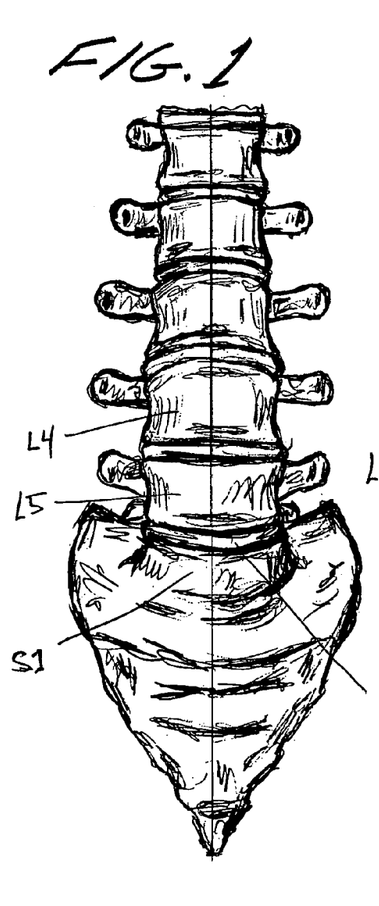
FIG. 1 is a fragmentary anterior view of a person's spine including L4, L5 and S1 vertebrae.
Figures 2, 3:
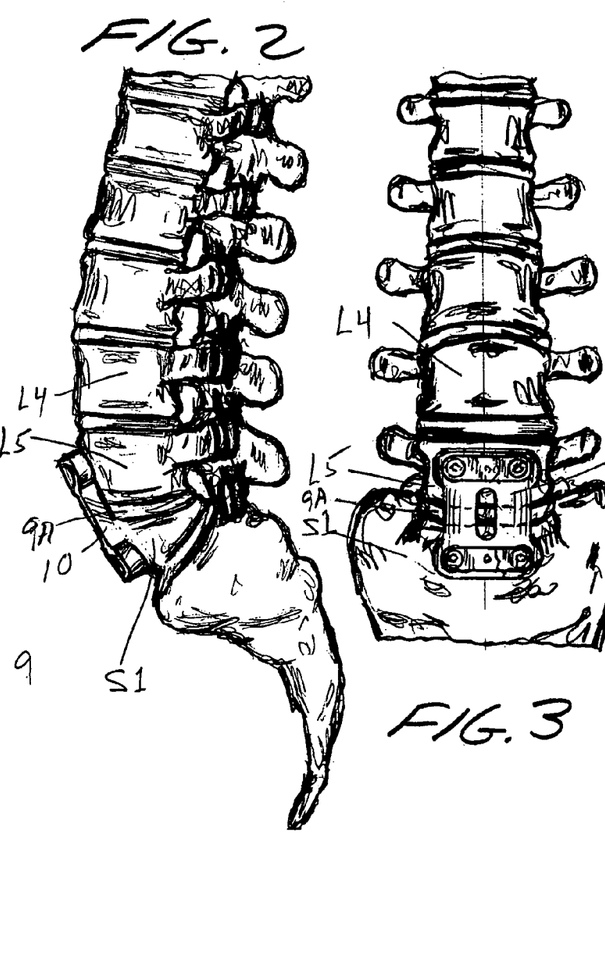
FIG. 2 is a side elevation view of the spine of FIG. 1, with the new lumbar plate in its implanted position adjacent L5 and S1 vertebrae.
FIG. 3 is a fragmentary anterior view of a person's spine showing the new lumbar plate implanted on L5 and S1 vertebrae.
Figure 4:
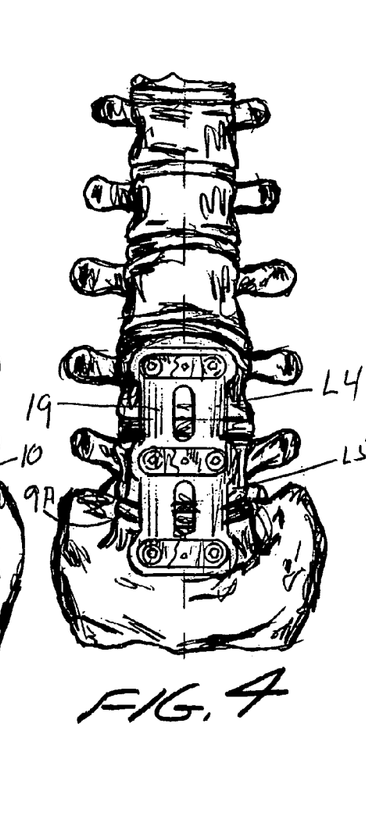
FIG. 4 is a view similar to that of FIG. 5, but showing a second embodiment of the new lumbar plate implanted on L4, L5 and S1 vertebrae.

FIG. 1 illustrates a portion of a person's vertebral column including L4,L5 and S1 vertebrae and disc 9 between L5 and S1. FIGS. 2 and 3 illustrate the same portion of a vertebral column with the new lumbar plate 10 installed onto L5,S1 and FIG. 4 illustrates the same vertebral column with a second embodiment 19 of the new lumbar plate installed onto L4,L5 and S1. In FIGS. 1, 3 and 4, the exposed visible surface of the vertebral column is the anterior surface, and in FIG. 2 the surface on the left side is the anterior surface. It is on these anterior surfaces of L4, L5 and S1 that the new lumbar plate is secured. As will be further explained below, where the new lumbar plate has been installed joining any two adjacent vertebrae, the disc between said vertebrae has been removed and replaced with a bone graft, indicated by reference number 9A in FIGS. 2-4, 18A and 18B.

Figure 5:
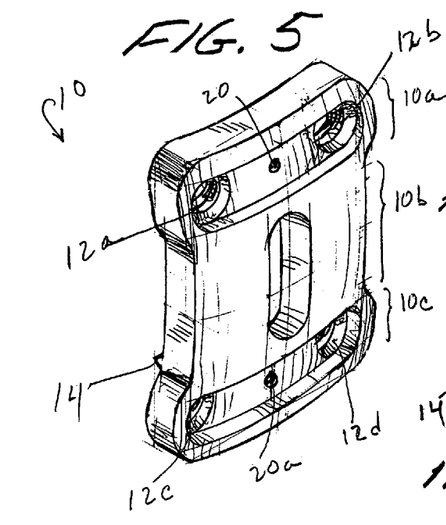
FIG. 5 is a top anterior perspective view of the new lumbar plate of FIGS. 1-3.
Figure 6:
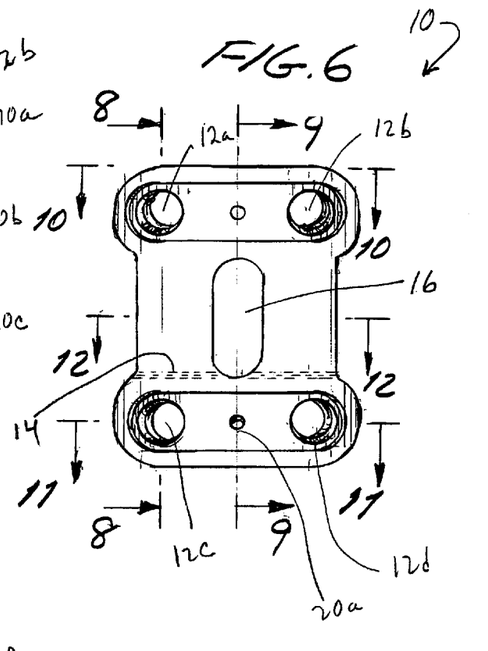
FIG. 6 is a front elevation view of the lumbar plate of FIG. 5.
Figures 7, 8, 9:
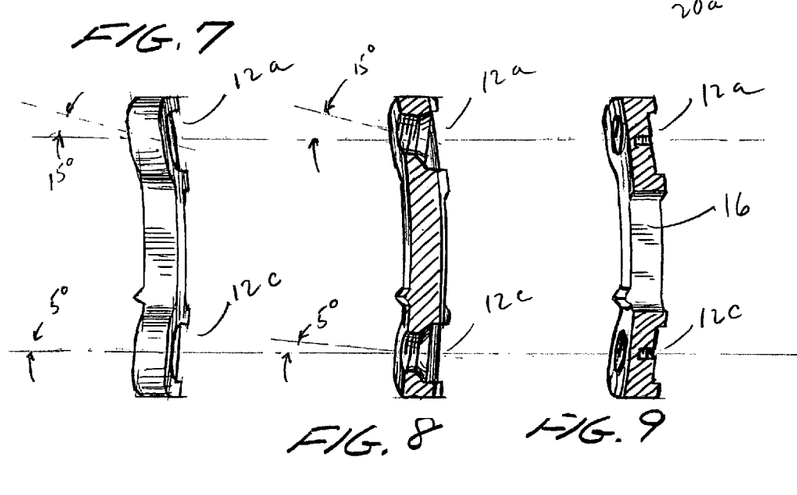
FIG. 7 is a left side elevation view of the lumbar plate of FIG. 6.
FIG. 8 is a sectional elevation view taken along lines 8-8 in FIG. 6.
FIG. 9 is a sectional elevation view taken along lines 9-9 in FIG. 6.

FIGS. 5-12 illustrate the structure of the first embodiment 10 of the new lumbar plate. As seen in the perspective view of FIG. 5 and the top plan view of FIG. 1, the plate has a concave curvature from left to right, and as seen in FIGS. 5 and 7, plate 10 has a concave curvature from top to bottom. Further, as seen in FIG. 5, new plate 10 has upper section 10a, middle section 10b and lower section 10c. In this upper section are spaced-apart bone screw holes 12a and 12b through which two bone screws are attachable to L5.

At the lower section 10c are spaced-apart holes 12c and 12d for receiving self-threading bone screws which are screwed into S1. FIGS. 7 and 8 show that holes 12a and 12b are inclined upward at an angle of 15° relative to a horizontal reference plane, these holes receiving the cephalad screws in upper section 10a. The central axis of the screw in hole 12c is generally perpendicular to plate 10 at the area where it traverses the plate, although the plate itself will be slightly curved.

Figures 17, 18A, 18B, 19, 20:
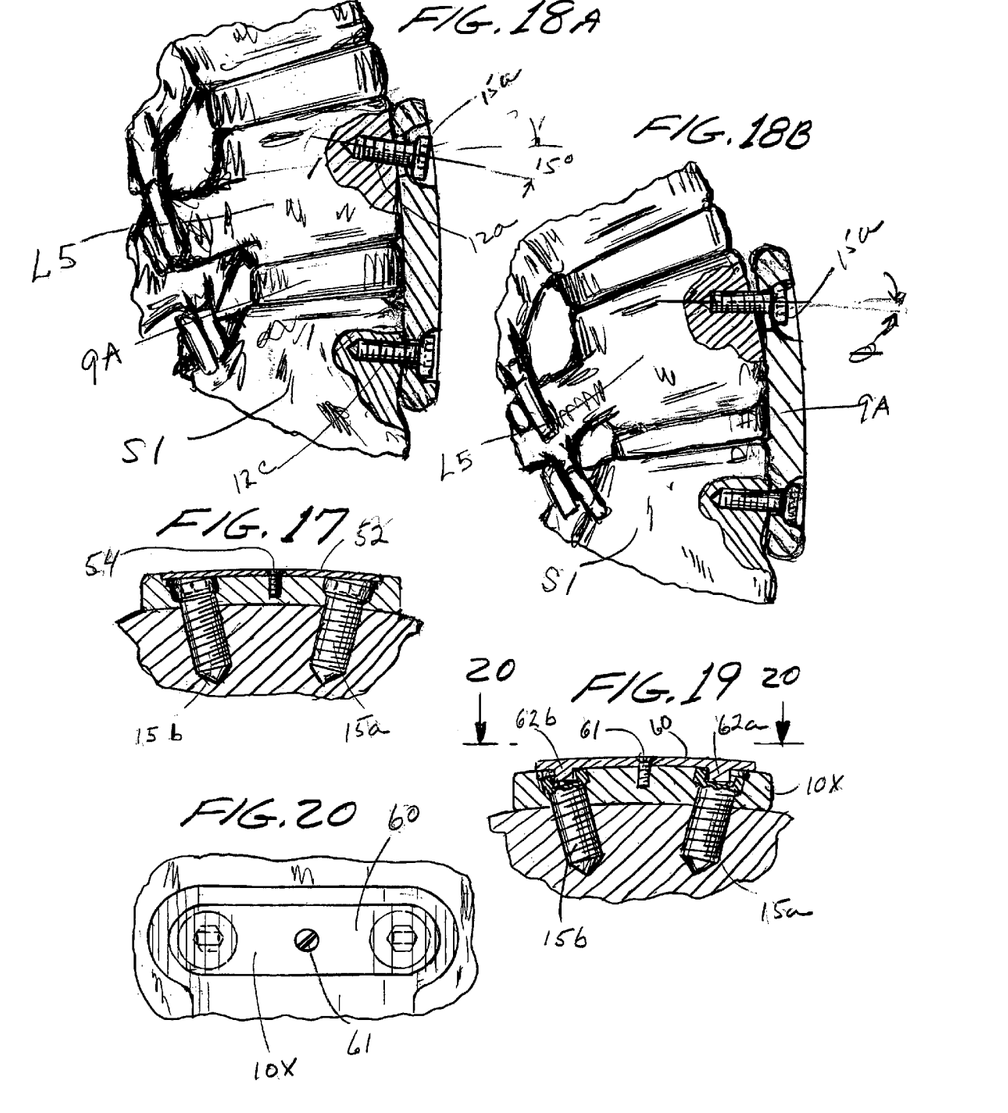
FIG. 17 is a side elevation view in section of the locking plate of FIG. 16 positioned on the lumbar plate.
FIG. 18A is a side elevation view, partially in section, of the lumbar plate initially secured to L5-S1 vertebrae, as seen in FIGS. 2 and 3, with upper bone screw 15a at an angle of approximately 15°.
FIG. 18B is a side elevation view, similar to FIG. 18A, showing the vertebrae and enclosed bone graft 9A in compression, with screw 15a in L5 moved downward to an angle which is less than the original 15°, (for clarity, the downward movement is of L5 and the compression of graft 9A is exaggerated)
FIG. 19 is a side elevation view, in section, of the second embodiment locking plate of FIG. 18 installed on a lumbar plate.
FIG. 20 is a top plan view of the locking plate of FIG. 19.

FIGS. 8, 17 and 19 show that each of holes 12a-12d is countersunk forming an internal shoulder. The bottom edge of each screw head engages said internal shoulder when the screw is driven into L5 or S1. Each of the unthreaded holes 12a through 12d are generally similar in size, namely about 6 mm in diameter for 5 mm diameter screws.

Figure 10:
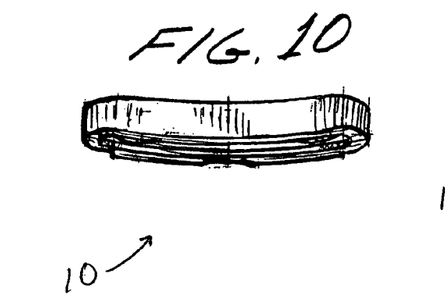
FIG. 10 is a top plan view of the lumbar plate in FIG. 6.
Figure 11:
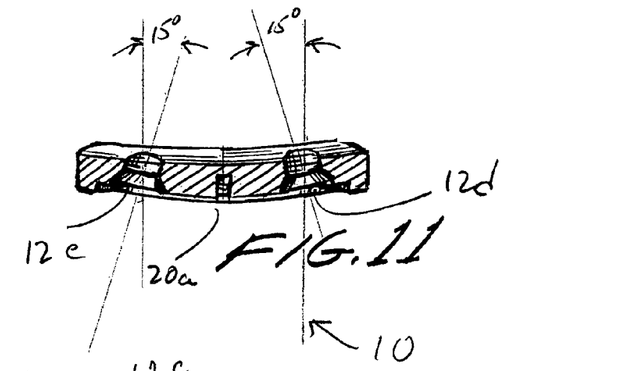
FIG. 11 is a sectional view taken along lines 11-11 in FIG. 6.
Figure 12:
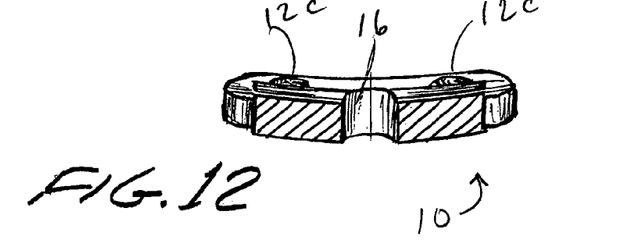
FIG. 12 is a sectional view taken along lines 12-12 in FIG. 6.

The two holes 12a and 12b in upper section 10a of the lumbar plate, as seen in FIGS. 7 and 8, are inclined upward at an angle of 15° and inclined inward at an angle of about 5° degrees, as seen in FIGS. 10 and 11.

As seen in FIGS. 2, 5, 6, 7, 8 and 9, this lumbar plate has a projecting rib or ridge 14 on the posterior side which engages the upper or superior edge on the anterior side of S1, which helps to properly locate the lumbar plate when it is positioned for hole drilling and screw attachment.

As seen in FIGS. 5, 6, 9 and 12, lumbar plate 10 has window aperture 16 extending generally vertically in the center of the plate between the upper and lower areas 10a and 10c. The function of this window is to permit the surgeon to see exactly where the plate is relative to the vertebral column, and to have access to the region behind the plate, while the surgery is taking place, and thereafter.

As seen in FIGS. 5, 6, 11, 13 and 14, on lumbar plate 10 between the holes 12a and 12b in the upper portion of 10a, is an additional hole 20 which is threaded to receive a 2 mm pan-head screw, although other screws may be used. This threaded hole serves two functions, namely, (a) to receive screw 32 that releasably secures the drill guide 30 to the lumbar plate, and (b) to receive screw 54 that releasably holds the locking plate 52 onto the lumbar plate to contact and prevent the bone screws from unscrewing, and more specifically, to prevent the heads of the bone screws from rising above and beyond the locking plate.

A. Drill Guide Assembly

FIGS. 13, 14, 14A, 14B and 15 illustrate the new drill guide assembly, as further described below. To enable the bone screws to be driven into L4 at the correct angle, which is inclined both vertically and horizontally, there is employed top drill guide 30 for the upper two holes and lower drill guide 40 for the lower two holes, as seen in FIGS. 13, 14, 14A, 14B and 15.

FIG. 8 shows that the upper holes 12a and 12b in the lumbar plate are each inclined 5° inwardly, and this applies similarly to the lower holes 12c and 12d. FIG. 14A demonstrates again that the upper holes 12a and 12b are inclined 15° upward relative to horizontal, while the lower holes 12c and 12d are inclined about 5° upward relative to horizontal.

Figure 13:
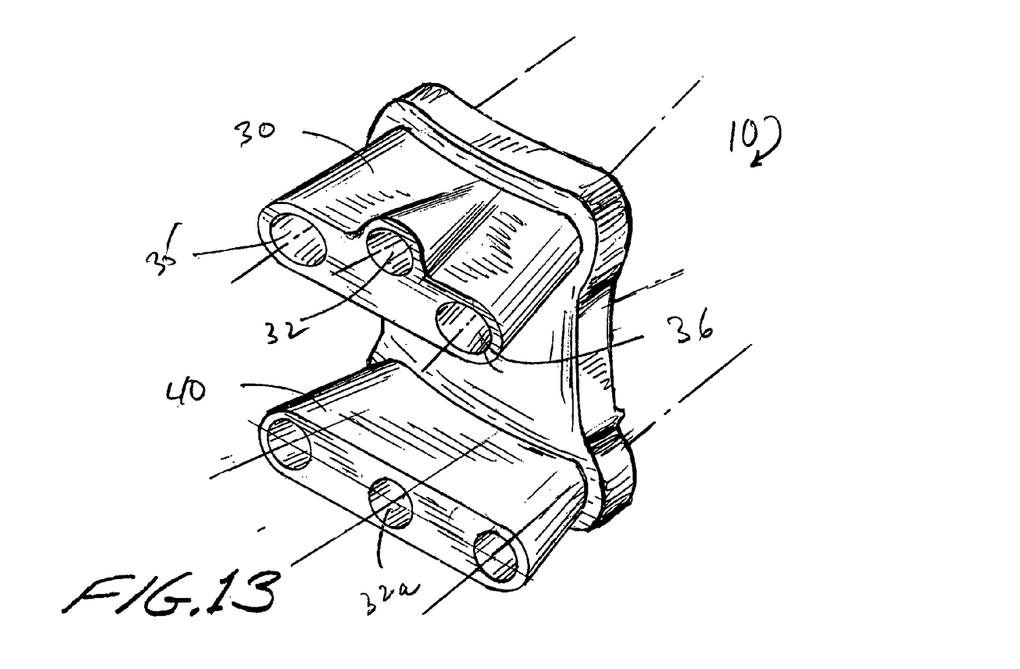
FIG. 13 is a top perspective anterior view of the lumbar plate of FIG. 5, with the top and bottom drill guides attached; however, in use only one of the drill guides would be attached at once.
Figures 14, 14A:
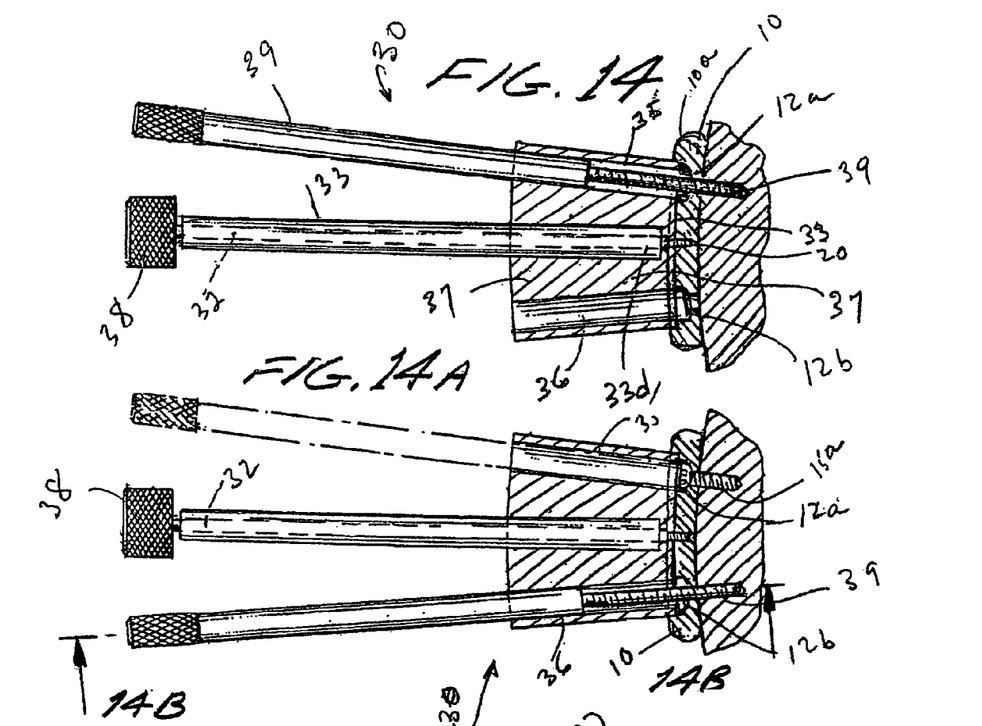
Figure 14B:
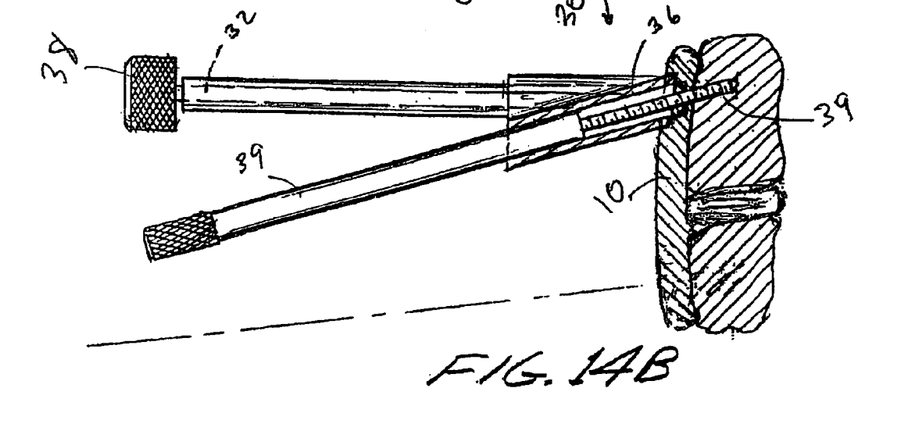
FIG. 14B is a side elevational view in section, taken along line 14B-14B in FIG. 14A, showing the top drill guide with a drill bit in upper right hole 12b.
Figures 15, 16, 18:
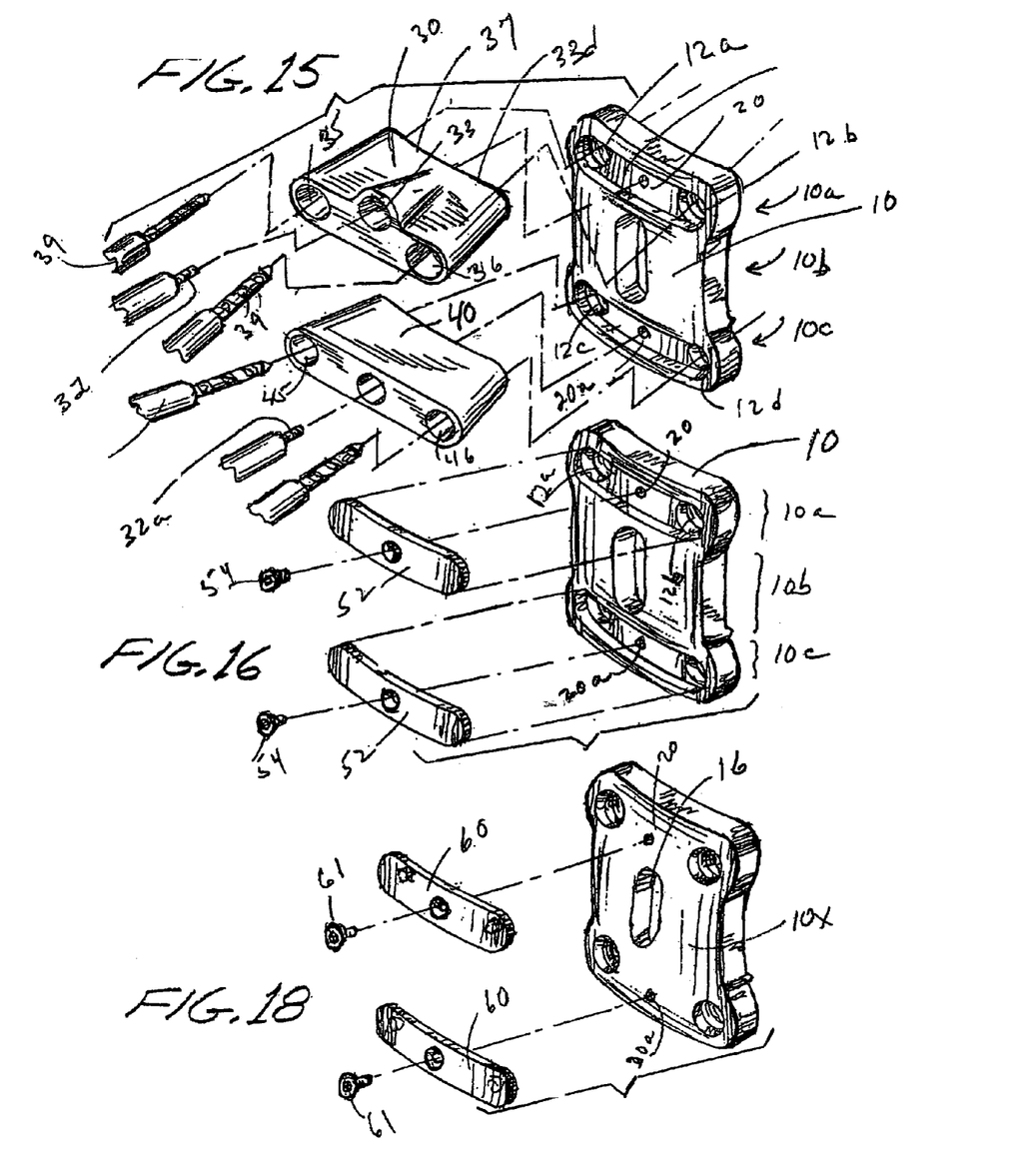
FIG. 15 is an exploded perspective view of the lumbar plate and drill guides, before either drill guide is attached to the lumbar plate.
FIG. 16 is an exploded perspective view of the lumbar plate with a first embodiment of the locking plate.
FIG. 18 is an exploded perspective view of the lumbar plate with a second embodiment of the locking plate.

As seen in FIGS. 14, 14A, 14B and 15, top drill guide 30 is releasably secured to lumbar plate 10 by screw 32 which extends downward through tube 33 into threaded hole 20 in the upper portion 10a of lumbar plate 20. Bottom drill guide 40 for the lower section 10c of lumbar plate 10 can be attached in a similar manner, as indicated in FIGS. 13 and 15, via screw 32a threadedly engaged in hole 20a in lower section 10c of lumbar plate 10. When top drill guide 30 is secured to lumbar plate 10 and such assembly is positioned firmly against L4 and S1 of the vertebral column, drill guide holes 35 and 36 of drill guide 30 will be aligned with lumbar plate holes 12a, 12b and will be inclined at the desired complex vertical and transverse angles, so that drill bit 39 can enter and correctly establish a properly oriented hole.

As seen in FIGS. 14, 14a, 14b and 15, screw 32 has an elongated form with a thumbscrew head 38 at the top for convenient rotation of this screw by the surgeon to releasably secure the drill guide 30 to lumbar plate 10. As shown in FIG. 14, this screw 32 extends through a guide tube 33 of top drill guide 30. By turning thumbscrew 38, the distal end 33d of tube 33 is urged downward in the bottom of a recess 50 in plate 10, which urges the web portion 37 of drill guide 30 tightly against lumbar plate 10.

The hole formation and bone screw installation is as follows. Top drill guide 30 is secured to lumbar plate 10 by screw 32 in hole 20, whereby holes 35, 36 of drill guide 30 are aligned with holes 12a, 12b of plate 10. Drill guide 30 establishes holes 35,36 at the proper angulation of about 15° upward and about 5° inward.

Next, this assembly of plate 10 plus drill guide 30 is positioned firmly against the anterior surface of L5-S1. Drill 39 is inserted through hole 35 and into L5 where a hole is formed. Drill 39 is withdrawn and screw 15a is installed. This procedure is repeated through hole 36 for installation of screw 15b in L5. Then screw 32 is withdrawn and top drill guide 30 is removed from plate 10. Next, while plate 10 remains secured to L5, drill guide 40 is secured by screw 32a to the lower portion 10c of plate 10. A similar drill and screw installation is followed to install screws 15c,15d in S1. Then, screw 32a is withdrawn and lower drill guide 40 removed from plate 10.

Next, x-rays are taken to confirm proper placement of screws 36a,36d. Next, locking plates 52 are installed to secure screws 36a,36d in their respective positions. Details of two embodiments of locking plates are described later.

B. Compression Loading of L5, S1 Vertebrae

As seen in FIGS. 2 and 3, the L5 and S1 vertebrae immediately above and below disk 9 will experience compression loading when the spine is generally upright. More specifically, L5 will try to move downward relative to S1; however, lumbar plate 10, if tightly screwed to both L5 and S1, will resist such relative movement. In the prior Synthese plate, discussed above, the upper and lower screws are threadedly engaged to the lumbar plate and thence threadedly engaged to L5 and S1. This arrangement essentially bars movement of L5 relative to S1, with the undesirable consequences of barring or reducing compression loading of these bones described above.

The present invention differs significantly from the Synthese plate, in that the new lumbar plate 10 has through holes 12a, 12b at the top and through holes 12c, 12d at the bottom, each having a bore diameter sufficient to allow L5 bone screws 15a, 15b and S1 bone screws 15c, 15d, to freely traverse these holes and to allow screws 15c, 15d to angulate up in L5 to about 15° from their original orientation relative to plate 10. The 12c, 12d holes provide only very slight clearance of about 1 mm, so that screws 15c, 15d can angulate only a small amount relative to the plate and to the axes of these holes.

FIG. 8A illustrates how screw 15a is situated, at the time of initial placement, at its maximal superior angulation, at an angle of about 15° upward; however, clearance allows this screw to toggle in the inferior direction (downward away from the head) when the downward load is applied by L5 and structure above. Such downward motion applies compression to the vertebrae and enclosed bone graft 9A, as indicated in FIG. 18, which enhances healing and bonding of the bone graft and adhesion of the screw within the vertebrae, thus leading to a more stable and secure union. For clarity, the amount of downward angulation of screw 15a and of compression of graft 9A is exaggerated in FIG. 18B.

If the elongated plate 19 is used to engage both L4 and L5, as seen in FIG. 4, the L4 and L5 screws would be installed at maximum superior angulation, while the S1 screws would still be installed at about 5° superiorly and still generally perpendicular to the plate.

C. Locking Plate

The first embodiment of the locking plate configuration is seen in FIGS. 16 and 17, and the second embodiment is in FIGS. 18, 19 and 20. As seen in FIG. 16, in upper portion 10a of lumbar plate 10 an elongated recess 50 overlies both holes 12a and 12b and the intermediate threaded hole 20. Above recess 50 is locking plate 52 having length, width and thickness dimensions corresponding generally to those of the recess or pocket 50, but slightly smaller so that locking plate 52 can fit down into pocket 50. Screw 54 releasably secures locking plate 52 in the pocket, with screw 54 threadedly engaging threaded hole 20. To insure that screw 54 will not accidentally become unscrewed, the proximal end of its threads near the head can be formed to have a pitch slightly different from the threads of hole 20. Final rotation of screw 54 will force these dissimilar threads into a frictional or interference fit with the threads of hole 20.

As seen in FIG. 17, when locking plate 52 is secured in recess 50, its ends overlay the heads of bone screws 15a and 15b in a manner that prevents these screws from becoming unscrewed. Where locking plate 52 contacts the top surface of the screws there is created both a frictional resistance to rotation of the screws, and furthermore plate 52 constitutes a barrier to bar the screws from moving axially out of the vertebrae.

FIGS. 18, 19 and 20 illustrate a second embodiment of the locking plate, namely plate 60 with its attachment screw 61 for engagement in threaded hole 20 of the lumbar plate 10x. FIG. 19 shows that the bottom of locking plate 60 has protrusions 62a, 62b. These protrusions extend down into the recess of the hex head screws 15a, 15b when the locking plate 60 is secured by screw 61 to the lumbar plate 10x. As with the previously described locking plate 52, when locking plate 60 is installed, it bars the screws 15a and 15b from unscrewing and rising axially, because the screw heads engage the bottom of the locking plate and cannot move axially, and because each protrusion 62a,62b extends into the recess of hex head screw 15a, 15b respectively.

D. Method of Employing the New Anterior Lumbar Lag Plate for Attachment to L4, L5, S1

The method of employing the new lumbar plate has been generally described in the above Summary of the Invention and in the section entitled Drill Guide Assembly, and further details follow. After the appropriate disc space is exposed and other preparation taken for attachment of a lumbar plate, the steps are as follows:

1. The plate length is determined by placing a plate template over the affected disc space and then choosing the appropriate length of lumbar plate, 2. The upper drill guide 30 is releasably affixed to upper portion 10a of lumbar plate 10 with thumbscrew 32.

3. Lumbar plate 10 with upper attached drill guide 30 is then placed upon the anterior surface of the adjacent vertebrae selected, which would be adjacent L4-S1 for the first embodiment of the new lumbar plate, 4. The two holes 35 and 36 in upper drill guide 30 are aligned with the two holes 12a, 12b in lumbar plate 10, which are now positioned correctly for forming holes in L4. A drill or awl is extended through the drill guide hole 36 and lumbar plate hole 12b and thence into L4 forming the hole therein. The drill or awl is then removed and a self-threading bone screw 15b is driven into hole 12b. Next, hole 12a is similarly formed via drill guide 30 and a self-threading bone screw 15a is installed. A typical bone screw into L5 extends through the lumbar plate hole 12a with sufficient clearance to allow about 15° of angulation of the screw relative to the plate. Consequently, during subsequent healing and bone regeneration, the slight movement or orientation change of the plate will allow loading on the vertebrae and bone graft to enhance the healing process and produce a more healthy and stronger resulting structure.

5. The top drill guide 30 is then removed from the lumbar plate by rotating the thumbscrew 38 which connects these two elements. As seen in FIG. 15, the lower drill guide 40 is then attached to lower portion 10c of the lumbar plate via screw 32a which is threadedly engaged into hole 20a in bottom region 10c of the lumbar plate. With this attachment, the drill holes 45 and 46 in the lower drill guide become aligned with holes 12c and 12d in the lumbar plate.

6. Next, holes are formed in S1, and self-threading bone screws 15c,15d are placed in these holes in the same manner that holes were formed and bone screws were placed in L5. Then, via screw 32a, the lower drill guide 40 is released and removed from the lumbar plate. Confirmation x-rays are taken to verify correct placement of the bone screws.

7. Finally, there is the placement of the locking plate 52 seen in FIGS. 16 and 17 or locking plate 60 as seen in FIGS.

18, 19 and 20. In either case, each locking plate is positioned onto the lumbar plate and secured there by threaded screw 54 for locking plate 52 or by screw 61 for locking plate 60. Each of these screws is preferably threadedly engaged into the same hole that was used to receive and hold the screw 32 for attaching a drill guide onto the lumbar plate.

As seen in FIGS. 16 and 17, locking plate 52 fits down into the recess or pocket 50, which results in a generally flush anterior surface of the lumbar plate. As seen in FIGS. 18 and 19 locking plate 60 can optionally be positioned externally and on top of lumbar plate 10x. Plate 60 is quite thin, but is still adequate to bar the screws 15a and 15b from becoming unscrewed.

As discussed earlier, the second embodiment 17 of the lumbar plate as seen in FIGS. 2, 4 and 6a is secured to L4, L5 and S1 in the same manner as described herein.

The lumbar plate and method of emplacement inventions described herein include features which may be combined in a variety of forms. The lag feature is achieved by allowing toggle, by clearance or other means, of the bone screws in the upper L5 or L5-L4 holes, sufficient to allow lag while still having the lag plate in secure engagement with L5 or L5-L4 and S1. The locking plate feature has utility and provides significant benefits, whether used in combination with the above-described lag feature or used on a conventional lumbar plate not capable of the lag feature. Such locking plate may be secured to the lumbar plate in a variety of ways.

A further embodiment of this invention is the combination of the lumbar plate with a first drill guide and/or with a second drill guide as described herein. A still further embodiment is the combination of the lumbar plate with the locking plate utilizing the same attachment hole in the lumbar plate for both the drill guide and for the locking plate. The lumbar plate described herein may be slightly bendable by the surgeon at the time of placement to better conform the plate to the curvature defined by L5-S1 or by L4-L5-S1. A further feature of the new lumbar plate is the inherently secure anchoring of the plate onto the L4-S1 vertebrae by virtue of the trapezoidal-like arrangement of the top and bottom bone screws, all inclined inwardly.

The above-described method of emplacement of the lumbar plate constitutes a still further embodiment, as regards the alignment and forming of the holes, placement of the screws and the attachment of the locking plates.

The present invention has been described in connection with the preferred embodiments. One of ordinary skill will be able to affect various alterations, substitutions or equivalents and other changes without departing from the broad concepts imparted herein. It is, therefore, intended that the patent issued hereon be limited only by the definitions contained in the appended claims and equivalents thereof.

The invention claimed is:

1. An anterior lumbar plate assembly attachable with bone screws to vertebrae of a person's spine, comprising:
    (a) a plate member having top, bottom and middle parts, anterior and posterior surfaces and laterally spaced side edges,
    (b) a first set of spaced-apart through holes in said top part extending through said plate member between said anterior and posterior surfaces;
    (c) a second set of spaced-apart through holes in said bottom part extending through said plate member between said anterior and posterior surfaces;
    (d) each of said through holes dimensioned to receive with clearance one of said bone screws and to engage and block passage of the head of said bone screw in the posterior direction;
    (e) a rib formed laterally across the posterior side of the plate member such that the rib's length between the laterally spaced side edges is its greatest dimension, the rib being located on the plate in a location such that the rib would engage a superior edge on the anterior side of the S1 vertebra and thereby properly locate the plate member for drilling of holes in the vertebrae for attachment of the plate member; and
    (f) at least one locking means on said plate member for restricting rotation of each of said bone screws from said vertebrae;
    wherein said top and bottom parts of said plate are curved toward said posterior side of said plate.

2. The anterior lumbar plate assembly according to claim 1, wherein said locking means comprises a plate releasably attached to said plate member and situated adjacent and anteriorly of the heads of said bone screws.

3. The anterior lumbar plate assembly according to claim 1, wherein said locking means restricts unscrewing of said bone screws.

4. The anterior lumbar plate assembly according to claim 3, wherein each of said bone screws has a socket head with a recess therein, and wherein said locking means comprises a plate with projections that extend posteriorly into said recesses of said screws to prevent movement thereof.

5. The anterior lumbar plate assembly of claim 1, wherein the rib is located on said bottom part of said plate member adjacent said second set of spaced-apart through holes.

6. An anterior lumbar plate assembly attachable with bone screws to vertebrae of a person's spine, comprising:
    (a) a plate member having top, bottom and middle parts, anterior and posterior surfaces and laterally spaced side edges,
    (b) a first set of spaced-apart through holes in said top part extending through said plate member between said anterior and posterior surfaces;
    (c) a second set of spaced-apart through holes in said bottom part extending through said plate member between said anterior and posterior surfaces;
    (d) each of said through holes dimensioned to receive with clearance one of said bone screws and to engage and block passage of the head of said bone screw in the posterior direction;
    (e) a rib formed on the posterior side of the plate member between the laterally spaced side edges such that the rib's length between the side edges is its greatest dimension, the rib being located on the plate in a location such that the rib would engage a superior edge on the anterior side of the S1 vertebra and thereby properly locate the plate member for drilling of holes in the vertebrae for attachment of the plate member; and
    (f) at least one locking mechanism on said plate member for restricting rotation of each of said bone screws from said vertebrae, the bone screws adapted to toggle within said clearance even upon locking of said locking mechanism;
    wherein said top and bottom parts of said plate are curved toward said posterior side of said plate.

7. The anterior lumbar plate assembly of claim 6, wherein said locking mechanism comprises a plate releasably attached to said plate member and situated adjacent and anteriorly of the heads of said bone screws.

8. The anterior lumbar plate of claim 6, wherein said locking mechanism restricts unscrewing of said bone screws.

9. The anterior lumbar plate assembly of claim 8, wherein each of said bone screws has a socket head with a recess therein, and wherein said locking mechanism comprises a plate with projections that extend posteriorly into said recesses of said screws to prevent movement thereof.

10. The anterior lumbar plate assembly of claim 6, wherein the rib is located on said bottom part of said plate member adjacent said second set of spaced-apart through holes.

11. An anterior lumbar plate assembly attachable with bone screws to vertebrae of a person's spine, comprising:
  (a) a plate member having top, bottom and middle parts, anterior and posterior surfaces and laterally spaced side edges,
  (b) a first set of spaced-apart through holes in said top part extending through said plate member between said anterior and posterior surfaces;
  (c) a second set of spaced-apart through holes in said bottom part extending through said plate member between said anterior and posterior surfaces;
  (d) each of said through holes dimensioned to receive with clearance one of said bone screws and to engage and block passage of the head of said bone screw in the posterior direction;
  (e) a rib formed laterally across substantially the entire posterior side of the plate member, the rib being located on the plate in a location such that the rib would engage a superior edge on the anterior side of the S1 vertebra and thereby properly locate the plate member for drilling of holes in the vertebrae for attachment of the plate member; and
  (f) at least one locking means on said plate member for restricting rotation of each of said bone screws from said vertebrae;
  wherein said top and bottom parts of said plate are curved toward said posterior side of said plate.

12. The anterior lumbar plate assembly of claim 11, wherein said locking means comprises a plate releasably attached to said plate member and situated adjacent and anteriorly of the heads of said bone screws.

13. The anterior lumbar plate of claim 11, wherein said locking means restricts unscrewing of said bone screws.

14. The anterior lumbar plate assembly of claim 13, wherein each of said bone screws has a socket head with a recess therein, and wherein said locking means comprises a plate with projections that extend posteriorly into said recesses of said screws to prevent movement thereof.

15. The anterior lumbar plate assembly of claim 11, wherein the rib is located on said bottom part of said plate member adjacent said second set of spaced-apart through holes.

16. An anterior lumbar plate assembly attachable with bone screws to vertebrae of a person's spine, comprising:
  (a) a plate member having top, bottom and middle parts, anterior and posterior surfaces and laterally spaced side edges,
  (b) a first set of spaced-apart through holes in said top part extending through said plate member between said anterior and posterior surfaces;
  (c) a second set of spaced-apart through holes in said bottom part extending through said plate member between said anterior and posterior surfaces;
  (d) each of said through holes dimensioned to receive with clearance one of said bone screws and to engage and block passage of the head of said bone screw in the posterior direction;
  (e) a rib formed laterally across the posterior side of the plate member such that the rib's length between the laterally spaced side edges is its greatest dimension, the rib being located on the plate in a location such that the rib would engage a superior edge on the anterior side of the S1 vertebra and thereby properly locate the plate member for drilling of holes in the vertebrae for attachment of the plate member; and
  (f) at least one locking means on said plate member for restricting rotation of each of said bone screws from said vertebrae;
  wherein only a single rib is formed laterally across the posterior side of the plate member.

17. The anterior lumbar plate assembly according to claim 16, wherein said locking means comprises a plate releasably attached to said plate member and situated adjacent and anteriorly of the heads of said bone screws.

18. The anterior lumbar plate assembly according to claim 16, wherein said locking means restricts unscrewing of said bone screws.

19. The anterior lumbar plate assembly according to claim 18, wherein each of said bone screws has a socket head with a recess therein, and wherein said locking means comprises a plate with projections that extend posteriorly into said recesses of said screws to prevent movement thereof.

20. The anterior lumbar plate assembly of claim 16, wherein the rib is located on said bottom part of said plate member adjacent said second set of spaced-apart through holes.

21. An anterior lumbar plate assembly attachable with bone screws to vertebrae of a person's spine, comprising:
  (a) a plate member having top, bottom and middle parts, anterior and posterior surfaces and laterally spaced side edges,
  (b) a first set of spaced-apart through holes in said top part extending through said plate member between said anterior and posterior surfaces;
  (c) a second set of spaced-apart through holes in said bottom part extending through said plate member between said anterior and posterior surfaces;
  (d) each of said through holes dimensioned to receive with clearance one of said bone screws and to engage and block passage of the head of said bone screw in the posterior direction;
  (e) a rib formed on the posterior side of the plate member between the laterally spaced side edges such that the rib's length between the side edges is its greatest dimension, the rib being located on the plate in a location such that the rib would engage a superior edge on the anterior side of the S1 vertebra and thereby properly locate the plate member for drilling of holes in the vertebrae for attachment of the plate member; and
  (f) at least one locking mechanism on said plate member for restricting rotation of each of said bone screws from said vertebrae, the bone screws adapted to toggle within said clearance even upon locking of said locking mechanism;
  wherein only a single rib is formed laterally across the posterior side of the plate member.

22. The anterior lumbar plate assembly of claim 21, wherein said locking mechanism comprises a plate releasably attached to said plate member and situated adjacent and anteriorly of the heads of said bone screws.

23. The anterior lumbar plate of claim 21, wherein said locking mechanism restricts unscrewing of said bone screws.

24. The anterior lumbar plate assembly of claim 23, wherein each of said bone screws has a socket head with a recess therein, and wherein said locking mechanism comprises a plate with projections that extend posteriorly into said recesses of said screws to prevent movement thereof.

25. The anterior lumbar plate assembly of claim 21, wherein the rib is located on said bottom part of said plate member adjacent said second set of spaced-apart through holes.

26. An anterior lumbar plate assembly attachable with bone screws to vertebrae of a person's spine, comprising:
(a) a plate member having top, bottom and middle parts, anterior and posterior surfaces and laterally spaced side edges,
(b) a first set of spaced-apart through holes in said top part extending through said plate member between said anterior and posterior surfaces;
(c) a second set of spaced-apart through holes in said bottom part extending through said plate member between said anterior and posterior surfaces;
(d) each of said through holes dimensioned to receive with clearance one of said bone screws and to engage and block passage of the head of said bone screw in the posterior direction;
(e) a rib formed laterally across substantially the entire posterior side of the plate member, the rib being located on the plate in a location such that the rib would engage a superior edge on the anterior side of the S1 vertebra and thereby properly locate the plate member for drilling of holes in the vertebrae for attachment of the plate member; and
(f) at least one locking means on said plate member for restricting rotation of each of said bone screws from said vertebrae;
wherein only a single rib is formed laterally across the posterior side of the plate member.

27. The anterior lumbar plate assembly of claim 26, wherein said locking means comprises a plate releasably attached to said plate member and situated adjacent and anteriorly of the heads of said bone screws.

28. The anterior lumbar plate of claim 26, wherein said locking means restricts unscrewing of said bone screws.

29. The anterior lumbar plate assembly of claim 28, wherein each of said bone screws has a socket head with a recess therein, and wherein said locking means comprises a plate with projections that extend posteriorly into said recesses of said screws to prevent movement thereof.

30. The anterior lumbar plate assembly of claim 26, wherein the rib is located on said bottom part of said plate member adjacent said second set of spaced-apart through holes.

* * * * *